United States Patent
Mineur

(10) Patent No.: US 7,041,833 B2
(45) Date of Patent: May 9, 2006

(54) 3-STEP SYNTHESIS OF PYRAZOLOTRIAZOLE COUPLERS AND COUPLER INTERMEDIATES

(75) Inventor: Catherine Mineur, Macedon, NY (US)

(73) Assignee: Eastman Kodak Company, Rochester, NY (US)

(*) Notice: Subject to any disclaimer, the term of this patent is extended or adjusted under 35 U.S.C. 154(b) by 64 days.

(21) Appl. No.: 10/830,644

(22) Filed: Apr. 23, 2004

(65) Prior Publication Data

US 2005/0240026 A1  Oct. 27, 2005

(51) Int. Cl.
*C07D 249/16* (2006.01)
*C07D 231/40* (2006.01)

(52) U.S. Cl. .................. 548/262.4; 548/375.1

(58) Field of Classification Search ............. 548/356.1, 548/360.5, 366.1, 371.4
See application file for complete search history.

(56) References Cited

U.S. PATENT DOCUMENTS 5,262,542 A  11/1993  Tang et al.
5,723,623 A  3/1998  Clarke et al.

FOREIGN PATENT DOCUMENTS

JP  8-69096  3/1996

OTHER PUBLICATIONS

Blake, et al. Synthesis and Chemistry of 3-tert-butyl-1,5-diaminopyrazole, Org. Biomol. Chem., vol. 1, pp. 4268-4274 (2003).*

* cited by examiner

*Primary Examiner*—Kamal A. Saeed
*Assistant Examiner*—Nyeemah Grazier
(74) *Attorney, Agent, or Firm*—Arthur E. Kluegel

(57) ABSTRACT

A process and intermediate useful for forming a 1H-Pyrazolo[1,5-b][1,2,4]triazole compounds comprise the step of reacting a 1,5-diaminopyrazole bearing a substituent, bonded to one and only one of the amine nitrogens by an acyl or thioacyl group, with a dehydrating agent in the presence of an aprotic solvent.

16 Claims, No Drawings

3-STEP SYNTHESIS OF PYRAZOLOTRIAZOLE COUPLERS AND COUPLER INTERMEDIATES

FIELD OF THE INVENTION

This invention relates to a method of preparing pyrazolotriazole compounds, which are useful as photographic dye forming couplers or as synthetic intermediates for the preparation of pyrazolotriazole photographic dye forming coupler compounds. In particular, it relates to a three-step method of preparing 1H-Pyrazolo[1,5-b][1,2,4]triazole compounds used in color photography form the corresponding aminopyrazole compound.

BACKGROUND OF THE INVENTION

It is known that pyrazolotriazole compounds are useful photographic dye forming couplers. Particularly, it is known in the art that 1H-Pyrazolo[1,5-b][1,2,4]triazole compounds are magenta dye forming couplers. Examples are EP 119, 860; U.S. Pat. No. 4,621,046; JP 62-172363; DE 19921733, and U.S. Pat. No. 5,998,122.

They are most commonly prepared through a multi-step procedure, as shown in Scheme 1. Examples are shown in JP 07-082252, U.S. Pat. No. 6,020,498, and U.S. Pat. No. 5,262,542.

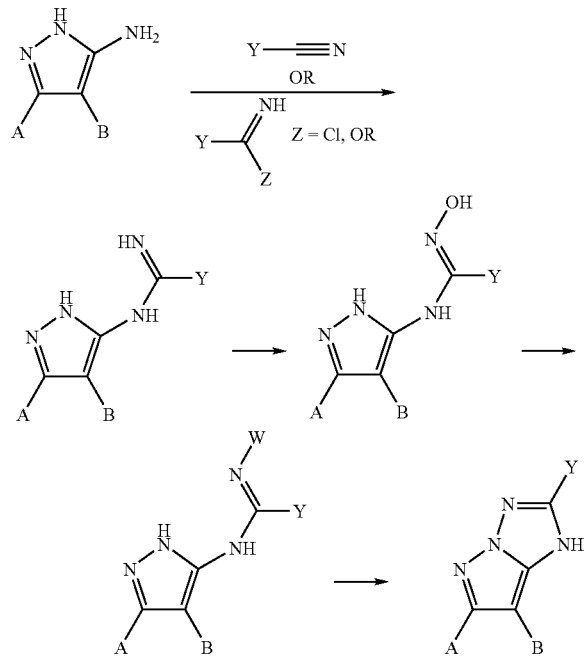

Scheme 1

These syntheses are long, comprising at least 4 steps. They require the use of nitrites or activated forms of amides as starting materials, some of which are toxic and/or not readily available.

There have been efforts to shorten the number of synthesis steps and increase yield and purity of these important intermediates for color photography. Recent examples are U.S. Pat. No. 6,555,711 and U.S. Pat. No. 6,657,066.

Prior art relating to diaminopyrazole compounds can be found in U.S. Pat. No. 5,723,623 and JP 08-069096 and [Sliskovic, D. R.; Siegel, M.; Lin, Y. I. *Synthesis*, 1986, 1, 71], and more recently in [Blake, A. J.; Clarke, D.; Mares, R. W.; McNab, H. *Org. Biomol. Chem.* 2003, 1, 4268]. The prior art reaction is pictured below, wherein E is a heteroatom (O, N or S) or heterogroup (a group connected by a O, N or S atom) and the reaction employed to close the ring requires the use of external heat and a base.

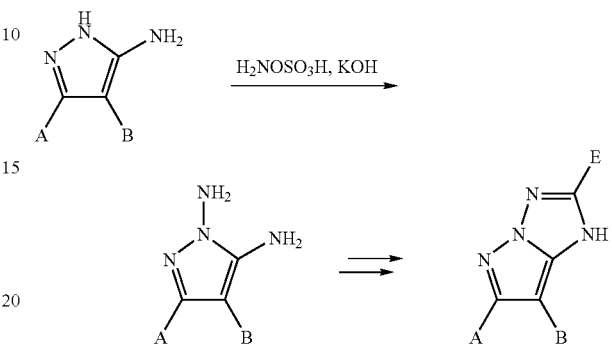

Scheme 2

The 1,5-diaminopyrazole compound and its synthesis are known in the art (see prior art described above, and a review of the use of the reagent hydroxylamine-O-sulfonic acid can be found at Wallace, R. G. Organic Preparations and Procedures Int. 14(4), 265–307, 1982).

It remains a problem to be solved to provide a synthesis for 1H-Pyrazolo[1,5-b][1,2,4]triazole compounds that can be carried out in fewer steps.

SUMMARY OF THE INVENTION

The invention provides a process that comprises the step of reacting a 1,5-diaminopyrazole bearing a substituent, bonded to one and only one of the amine nitrogens by an acyl or thioacyl group, with a dehydrating agent in the presence of an aprotic solvent whereby a 1H-Pyrazolo[1,5-b][1,2,4]triazole compound is formed. It also provides a useful intermediate.

The invention provides a finished product in fewer steps than in the known methods.

DETAILED DESCRIPTION OF THE INVENTION

The invention is summarized above. This invention provides an alternate synthesis of a 1H-Pyrazolo[1,5-b][1,2,4]triazole compound, as shown in Scheme 2 (with the group or atom E being a carbon or carbon-based substituent), comprising only two steps when starting from the 1,5-diaminopyrazole compound or three steps starting from the aminopyrazole compound.

The entire reaction sequence is represented by the following Scheme 3:

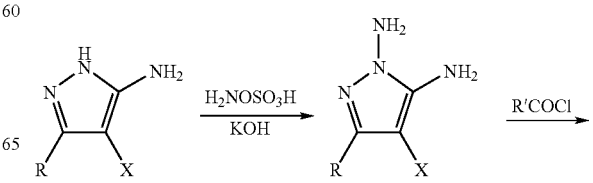

Scheme 3

-continued

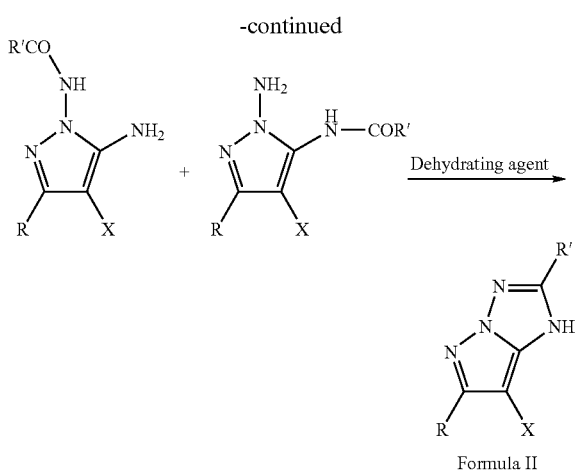

Formula II

Isomer mixture will be represented in the remaining document as Compound of Formula I, as below, where J, K = H, COR' or COR', H.

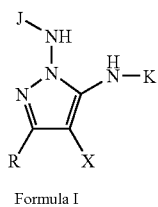

Formula I

The diaminopyrazole compound and its synthesis are known in the art. The 1,5-diamino compound in excess is slowly added to the acylating agent, such as an acid chloride or any other activated form of carboxylic acid to form monoamides of formula I, often obtained as an isomeric mixture. In some cases, the bis-amide compound, where both exocyclic nitrogen atoms are reacted with the acid chloride, cannot be avoided but can be separated from the monoamides during the purification. After purification, the monoamides are cyclized by reaction with a dehydrating agent in the presence of a solvent to form the desired pyrazolotriazole compounds.

The shorter synthetic pathway, as well as the greater availability and the lower toxicity of acylating agents such as acid chlorides, acid anhydrides, or their carboxylic acid parents are great advantages over the usual preparation routes to the desired pyrazolotriazole compounds.

The cyclization reaction is represented by the following Scheme 4:

Scheme 4

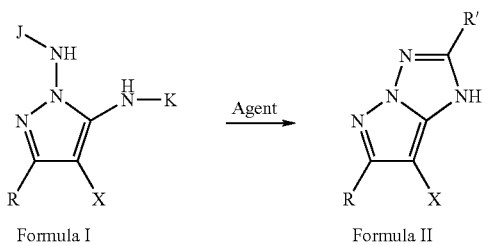

Formula I          Formula II

Compounds of Formula I (R, X, J, K, and R' are as defined below) are reacted with the dehydrating compound in the presence of a solvent.

The dehydrating agent may be any such agent such as those described in *Comprehensive Organic Chemistry—The Synthesis and Reactions of Organic Compounds*, Barton, D.; Ollis, D.; Vol VI, pp. 888–889, Pergamon Press, ISBN 0-08-022931-6. Useful agents include phosphorus pentoxide, phosphorus pentachloride, thionyl chloride and phosphorus oxychloride. Conveniently phosphorus pentachloride or phosphorus oxychloride are employed. In the case of the oxychloride, it is desirable in most instances to add a base to promote the reaction in a desired time. Any base that does not interfere with the reaction may be employed. Aromatic amines such as pyridine are suitable for this purpose.

The solvent may be any aprotic solvent such as those described in *Solvents and Solvent Effects in Organic Chemistry*, Reichardt, R.; pp 66 and 76, VCH (NY), ISBN 0-89573-661-6. Useful solvents include aromatic or aliphatic solvents such as benzene or heptane, methylene chloride, acetonitrile. Typically, toluene is used.

Substituents R, X, J, K, and R' in compounds are defined as follows:

R is a substituent group or H. R may be selected from one of the following groups, for example, an alkyl; alkoxy; alkylthio; aryl; aryloxy; arylthio; heterocyclyl; acyl (alkyl- or aryl-carbonyl); carboxylic acid or ester (alkoxy- or aryloxy-carbonyl); primary, secondary, tertiary amino (alkyl- or aryl-amino); primary or secondary amido (alkyl- or aryl-amido); sulfonamido (arlkyl- or aryl-sulfonamido); sulfinyl (alkyl- or aryl-sufinyl); sulfamoyl (alkyl- or aryl-sulfamoyl); carbamoyl (alkyl- or aryl-carbamoyl); and cyano groups. Convenient embodiments of R include alkyl and alkoxy groups having from 1 to 18, preferably 1 to 4, carbon atoms; phenyl or phenyloxy, and cyano groups. Typically, R is an alkyl; a t-alkyl group having from 4 to 10 carbon atoms e.g. t-butyl, adamantyl, t-pentyl; or a phenyl group.

X is hydrogen, or an acyl, or a heterogroup (a halogen or a group connected by a P, S, O or N atom such as a coupling-off group known to those skilled in the photographic art). Examples include halogen, particularly chlorine, bromine, or fluorine, alkoxy, aryloxy, heterocyclyl, heterocyclyloxy, heterocyclylimido, heterocyclylthio, sulfonyloxy, acyloxy, carbonamido, imido, acyl, thiocyano, alkylthio, arylthio, sulfonamido, phosphonyloxy, and arylazo groups. Examples of X groups are —Cl, —Br, —F, —SCN, —OCH$_3$, —OC$_6$H$_5$, —OSO$_2$CH$_3$, —S(CH$_2$)$_2$CO$_2$H, and —P(=O)(OC$_2$H$_5$)$_2$. Preferably, X is hydrogen or halogen, and more preferably H or Cl.

J and K are defined in relation to each other: If J is a substituent, K must be hydrogen. If K is a substituent, J must be hydrogen. The substituent mentioned for J or K is defined as acyl —(C=O)—R' (R' being C$_2$–C$_{20}$ alkyl; aryl; or heterocyclyl group); or thioacyl (C=S)—R' (R' defined as above). Examples of useful R' groups are alkyl (at the exclusion of Methyl); substituted alkyl; branched alkyl; and substituted phenyl groups. Typical embodiments of R' are substituted aryl groups, such as meta-nitro- or para-nitrophenyl groups.

The reaction conditions are not particularly critical. Temperatures in the range of 10–150° C., desirably 18° C. to reflux, typically higher than 50° C. Reaction times in the range of 1 to 2 hours are usually sufficient, but shorter or longer times may be used depending on other conditions.

Diaminopyrazole Preparation

Another embodiment of the invention provides an improvement in the preparation and isolation of diaminopyrazole compounds of Formula I (J and K being both hydrogen atoms)

Diaminopyrazole compounds can be synthesized from the aminopyrazole with the commercially available reagent hydroxylamine-O-sulfonic acid, in any organic solvent, under basic conditions, at a temperature, at a temperature between −10° C. and 70° C.

Diaminopyrazole compounds (R=alkyl; t-alkyl, as defined above; phenyl and X=hydrogen; halogen) are obtained in particularly suitable solvents such as dimethylformamide, dimethylacetamide, methanol, ethanol, isopropanol, acetonitrile, toluene, or any mixture of these solvents, at a temperature between −10° C. and 20° C. Preferred bases are inorganic bases such as sodium hydroxide, potassium hydroxide, potassium carbonate. Diaminopyrazole compounds can be isolated as free bases or as their ammonium salts.

Preferred embodiments are when X=chloro; the reaction is done at a temperature between 0 and 10° C., in dimethylformamide or dimethylacetamide, pure or in mixture with a solvent such as toluene, in the presence of a strong base such as sodium hydroxide or potassium hydroxide. The diaminopyrazole compounds are isolated as their hydrochloride salts or as their methanesulfonate salts.

Monoamide Preparation

A further embodiment of the invention provides an improved preparation for compounds of Formula I (R, X, J and K as defined above): Compounds of Formula I can be obtained by reacting the known diaminopyrazole (with R and X as defined above) with the carboxylic acid R'CO$_2$H (R' as defined above) in the presence of a coupling agent (such as 1,3-dicyclohexylcarbodiimide or carbonyldiimidazole) or of a chlorinating agent (such as phosphorus trichloride); or with a reactive form thereof, such as an acid chloride or an acid anhydride; in the presence of a solvent; at a temperature comprised between −20° C. and reflux. A base can be used but is not necessary.

Examples of reaction conditions are the use of an excess of the acid chloride or the acid anhydride; in a solvent such as toluene, ethyl acetate or acetonitrile, at a temperature comprised between 20° C. to reflux; or the use of an excess of the aminopyrazole in a solvent such as toluene, ethyl acetate or acetonitrile, at a temperature comprised between −10° C. and 40° C.

Preferable reaction conditions are a slow addition of the acid chloride R'COCl (R' defined as above) to a two-equivalent excess of the diaminopyrazole (R and X defined as above), in a solvent such as ethyl acetate or acetonitrile; at room temperature; followed by an acidic work-up of the reaction mixture.

Some representative compounds of diaminopyrazoles of Formula I are:

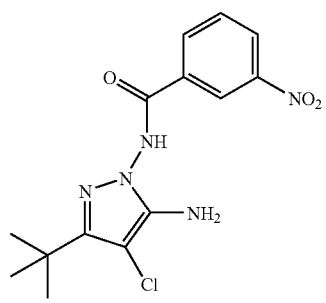

-continued

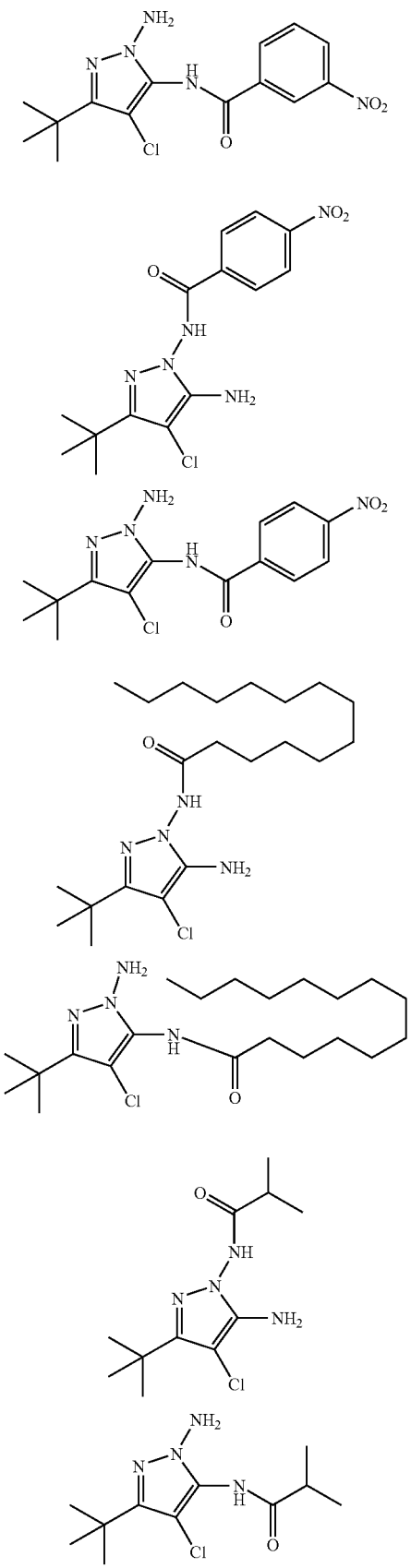

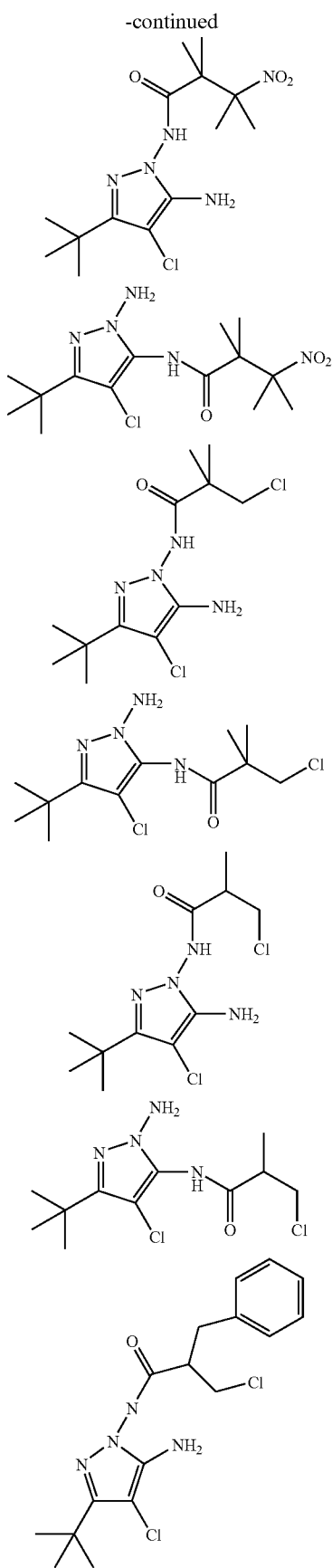
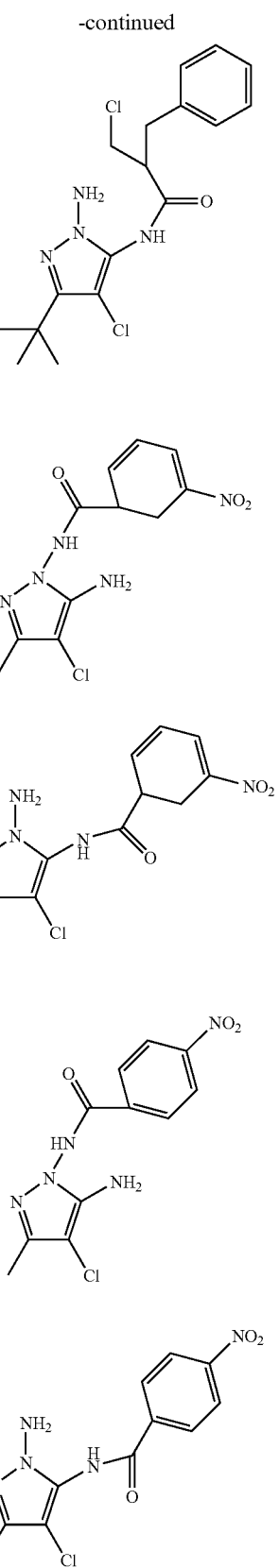
Some examples of representative pyrazolotriazole compounds of Formula II are as follows:

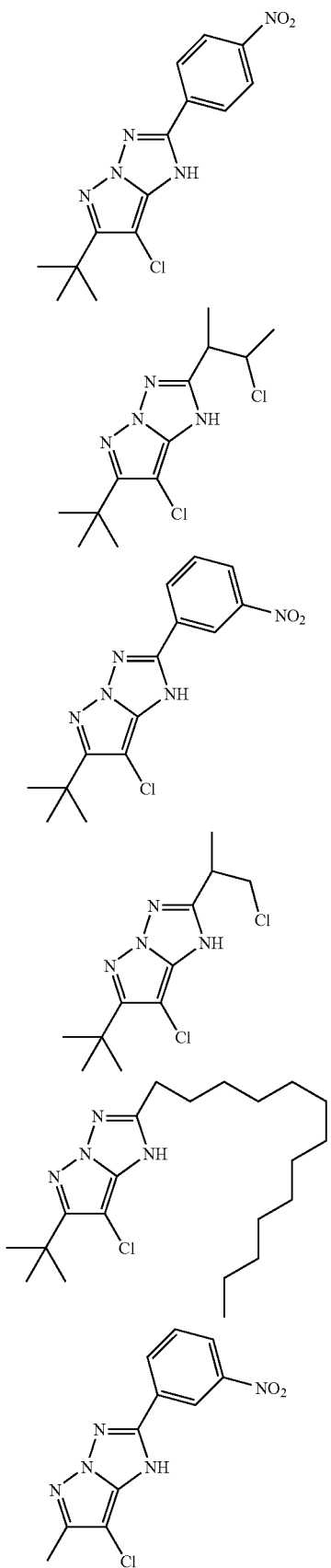

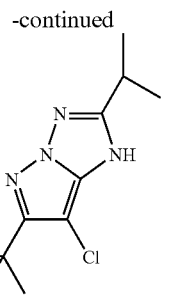

-continued

Unless otherwise specifically stated, use of the term "substituted" or "substituent" means any group or atom other than hydrogen. Unless otherwise provided, when a group, compound or formula containing a substitutable hydrogen is referred to, it is also intended to encompass not only the unsubstituted form, but also form further substituted with any substituent group or groups as herein mentioned, so long as the substituent does not destroy properties necessary for utility. Suitably, a substituent group may be halogen or may be bonded to the remainder of the molecule by an atom of carbon, silicon, oxygen, nitrogen, phosphorous, or sulfur. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, cyclohexyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentylphenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxopyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, hydrophobic groups, solubilizing groups, blocking groups, and releasing or releasable groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

Preparation of Compounds of Formula I—Selective Mono-Amidation:

A detailed description of the preparation of compounds of Formula I can be found in following examples 2 and 3. When R=t-butyl, X=chloro, R' in groups J or K is substituted aryl, the monoamide compounds can be prepared by reacting an excess of the acid chloride or the acid anhydride in a solvent such as toluene, ethyl acetate or acetonitrile, at a temperature comprised between 20° C. to reflux. The main product will be the bis-amide (where J and K are both substituted with an acyl group). It can be selectively hydrolyzed to a monoamide by treatment with a 10% solution of potassium hydroxide in methanol, under reflux conditions for up to 24 h. The monoamide compounds can be purified by a column chromatography.

For most amide compounds, the easiest preparation consists of reacting an excess of the diaminopyrazole compound with the acid chloride compound at a temperature close to room temperature, the excess of diaminopyrazole compound being removed after reaction by an acidic aqueous work-up.

The compounds of formula I (R, X, J and K as defined above) can be obtained after the work-up, as a single isomer or as an isomeric mixture, by simple solvent evaporation, or they can be isolated and purified by crystallization or by chromatography. The main side-product is the bis-amide compound of Formula I, with R and X defined as above, J and K both bearing a substituent COR', R' as defined above. It is usually separated by chromatography from the desired compounds of Formula I (R, X defined as above, J or K bearing an acyl substituent as defined above).

In some cases (especially when R=t-butyl, X=chloro, J or K is —(C═O)-3-nitrophenyl), the selectivity in forming one isomeric amide is very high, and both the bis-amide compound as well as the minor amide isomer compound can be separated from the major compound by crystallization.

Reaction of Compounds of Formula I—Preparation of Compounds of Formula II

A detailed description of the reaction can be found in the following examples 4 and 5. Compounds of Formula I, with J or K being a trisubstituted alkyl acyl group, do not react well under the described conditions. The main side-product of the ring-closure reaction with phosphorus pentachloride or phosphorus oxychloride is usually a bis-amide compound, which is mostly observed when compounds of Formula I (with R, X, J, K as defined above, R' being an unsubstituted alkyl group) are reacted. The compound of Formula II is usually purified by chromatography.

EXAMPLES

In the following are described the preparation of intermediates of the invention, like the diaminopyrazole (Example 1), some representative compounds of Formula I (Examples 2, 3, 4) and some representative pyrazolotriazole compounds obtained using the invention (Examples 5 and 6).

Example 1

Preparation of the diaminopyrazole of Formula I (R=t-butyl, X=chloro, J=K=H), with Isolation as its methanesulfonate ammonium Salt A 1 L jacketed flask was loaded at 20° C. with 50.00 g (0.288 mol) of aminopyrazole (R=t-butyl, X=chloro), 400 mL of toluene, 250 mL of dimethylformamide, 148.00 g (2.25 mol) of 85 w % of potassium hydroxide pellets, mechanically stirred and cooled to 10° C. After 30 minutes, 69.11 g (0.55 mol) of hydroxylamine O-sulfonic acid was added by portions over 1 h. At the end of the addition, the mixture was stirred for 30 min. at 10° C., then warmed up to 20° C., diluted with ethyl acetate, washed with an aqueous solution of 5% HCl, then a solution of salt and water (while keeping the aqueous layer basic). The organic layer was separated, and concentrated under vacuum. 300 mL of fresh toluene were added, the solution was clarified, and 27.96 g (0.29 mol) of methanesulfonic acid was slowly added at 20° C. The precipitation was completed overnight in the fridge. The yellow solid was collected, washed with toluene, air-dried for 2 h, dried in vacuum-oven at 40° C. for 3 days (25 in. Hg, under $N_2$ sweep) to a recovered 73.68 g of a light yellow powdery solid (90.0% of theoretical yield). The assay by gas chromatography (on the free base) was 95 area %. An analysis of the volatiles showed that up to 3.6 w % of water could be present. No solvent or excess acid could be detected.

Example 2

Formula I, with R=t-butyl, X=chloro, J or K=COR', R'=3-nitrophenyl

A solution of 10.00 g (0.0352 mol) of diaminopyrazole methanesulfonate ammonium salt, as obtained in Example 1, was stirred at 20° C. in 50 mL of ethyl acetate with an aqueous solution of sodium hydrogen carbonate until complete solubilization occured. The layers were separated, and the organic layer was dried over sodium sulfate, filtered and concentrated under vacuum. A solution of the residue in 20 mL of ethyl acetate was prepared and stirred at 20° C., to which 3.63 g (0.0196 mol) of 3-nitrobenzoyl chloride in solution in 60 mL of ethyl acetate was added slowly at 20° C. The resulting mixture was stirred overnight. The precipitate was collected, rinsed with ethyl acetate, stirred in a mixture of 80 mL ethyl acetate with 100 mL water until complete solubilization occurred to which 30 mL of 10% aqueous HCl was slowly added. The layers were separated and the organic layer was washed with 10% HCl, 5% sodium hydrogen carbonate and brine, dried over sodium sulfate, concentrated under vacuum, and dried under vacuum to give 3.75 g (56.7% of theoretical) of compound of Formula I (R, X, J and K as defined).

Example 3

Formula I (R=t-butyl, X=chloro, J or K=COR', R'=para-nitrophenyl)

A solution of 6.88 g (0.02425 mol) of diaminopyrazole methanesulfonate ammonium salt, as obtained in Example 1, was stirred at 20° C. in 40 mL of ethyl acetate with an aqueous solution of sodium hydrogen carbonate until complete solubilization occurred. The layers were separated, and the organic layer was dried over sodium sulfate, filtered and concentrated under vacuum. A solution of the residue in 15 mL of ethyl acetate was prepared and stirred at 20° C., to which a solution of 4-nitrobenzoyl chloride (2.50 g, 0.0135 mol) in 60 mL EtOAc was added over 3 h. The resulting mixture was stirred overnight at 20° C., diluted with ethyl acetate, washed four times with dilute HCl in water, dried over potassium carbonate, filtered and concentrated under vacuum. The residue was purified by column chromatography on silica gel (eluent: ethyl acetate—heptane 40–60).

The compounds of Formula I as defined above were further purified by recrystallization to lead to a recovered 84% yield. The mono-amide isomeric ratio was of 6:1 in the reaction mixture.

Example 4

Formula II, with R=t-butyl, X=chloro, R'=m-nitrophenyl

A solution of 0.5 g (0.00148 mol) of compound of Formula I (with R=t-butyl, X=chloro, J or K=COR', with R'=m-nitrophenyl) in 10 mL toluene was heated to reflux with 0.31 g (0.00148 mol) of phosphorus pentachloride for 1 h then cooled down to room temperature, diluted with ethyl acetate, washed with sodium carbonate, brine. The organic layer was separated, dried over sodium sulfate, filtered, and concentrated to dryness. This residue was chromatographed on silica gel to a recovered 0.15 g (32% of theoretical yield) of pure material.

Example 5

Formula II, with R=t-butyl, X=chloro, R'=m-nitrophenyl

To a solution of 0.53 g (0.00157 mol) of compound of Formula I (with R=t-butyl, X=chloro, J or K=COR', with R'=m-nitrophenyl) and 0.48 g (0.0031 mol) of phosphorus oxychloride in 10 mL toluene was slowly added 1.6 g of pyridine (0.0157 mol). This mixture was refluxed for 2 h then cooled down to room temperature, diluted with ethyl acetate, washed with aqueous sodium hydroxide, then 10% aqueous hydrochloric acid. The organic layer was separated, dried over sodium sulfate, filtered, concentrated to dryness. This residue was chromatographed on silica gel to a recovered 0.20 g (40% of theoretical yield) of pure material.

Example 6

Formula II, with R=t-butyl, X=chloro, R'=p-nitrophenyl

To a slurry of 0.25 g (0.00074 mol) of compound of Formula I (with R=t-butyl, X=chloro, J=COR', with R'=p-nitrophenyl, K=H) and 0.11 g (0.00074 mol) of phosphorus oxychloride in 10 mL toluene was slowly added 0.6 mL of pyridine (0.0157 mol). This mixture was refluxed for 1.5 h then cooled down to room temperature, diluted with ethyl acetate, washed with aqueous sodium hydroxide, then 10% aqueous hydrochloric acid. The organic layer was analyzed by LC and LC-MS and showed the complete disappearance of the compound of Formula I and the presence of the desired compound of Formula II, which was not isolated.

Example 7

Formula II, with R=t-butyl, X=chloro, R'=p-nitrophenyl

To a slurry of 0.25 g (0.00074 mol) of compound of Formula I (with R=t-butyl, X=chloro, J=H, K=COR', with R'=p-nitrophenyl) and 0.11 g (0.00074 mol) of phosphorus oxychloride in 10 mL toluene was slowly added 0.6 mL of pyridine (0.0157 mol). This mixture was refluxed for 1.5 h then cooled down to room temperature, diluted with ethyl acetate, washed with aqueous sodium hydroxide, then 10% aqueous hydrochloric acid. The organic layer was analyzed by LC and LC-MS and showed the complete disappearance of the compound of Formula I and the presence of the desired compound of Formula II, which was not isolated.

What is claimed is:

1. A process comprising the step of reacting a 1,5-diaminopyrazole bearing a substituent, bonded to one and only one of the amine nitrogens by an acyl or thioacyl group, with a dehydrating agent in the presence of an aprotic solvent whereby a 1H-Pyrazolo[1,5-b][1,2,4]triazole compound is formed, the reaction being represented by the equation:

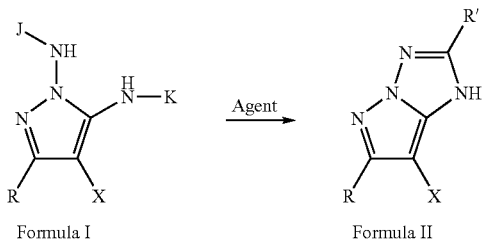

Formula I        Formula II wherein one of J and K is H and the other is an acyl or thioacyl group, R is H or a substituent group, and X is H, acyl, halogen or a group connected by a heteroatom of P, S, O, or N.

2. The process of claim 1 wherein the acyl or thioacyl group is an acyl group.

3. The process of claim 1 wherein the acyl or thioacyl group is a thioacyl group.

4. The process of claim 1 wherein the dehydrating agent comprises one selected from the group consisting of phosphorus peroxide, phosphorus pentachloride, thionyl chloride and phosphorus oxychloride.

5. The process of claim 1 wherein the dehydrating agent comprises one selected from the group consisting of phosphorus pentoxide and phosphorus oxychloride.

6. The process of claim 1 wherein the aprotic solvent comprises an aromatic or aliphatic solvent.

7. The process of claim 1 wherein the aprotic solvent comprises one selected from the group consisting of toluene, benzene, heptane, methylene chloride, and acetonitrile.

8. The process of claim 1 wherein the aprotic solvent comprises toluene.

9. The process of claim 1 additionally comprising a base.

10. The process of claim 9 wherein the base comprises an organic base.

11. The process of claim 10 wherein the organic base comprises pyridine.

12. The process of claim 11 wherein the dehydrating agent comprises phosphorus oxychloride.

13. The process of claim 1 wherein the 1,5-diaminopyrazole bearing a substituent is obtained by reacting a diaminopyrazole with a an acid chloride in a mole ratio of at least 1.5 to 1.

14. The process of claim 13 wherein the diaminopyrazole is formed by the step of reacting a monoaminopyrazole with hydroxylamine-o-sulfonic acid in an organic solvent.

15. The process of claim 14 wherein the diamino compound is separated by forming the methanesulfonic acid salt of the compound and filtering to recover the diamino compound.

16. The process of claim 1 wherein X is a halogen.

* * * * *

UNITED STATES PATENT AND TRADEMARK OFFICE
CERTIFICATE OF CORRECTION

| | |
|---|---|
| PATENT NO. | : 7,041,833 B2 |
| APPLICATION NO. | : 10/830644 |
| DATED | : May 9, 2006 |
| INVENTOR(S) | : Catherine Mineur |

It is certified that error appears in the above-identified patent and that said Letters Patent is hereby corrected as shown below:

Col. 15, Claim 4, line 26, delete "peroxide" and insert --pentoxide--.

Signed and Sealed this

Fifth Day of December, 2006

JON W. DUDAS
*Director of the United States Patent and Trademark Office*